(12) United States Patent
Williamson et al.

(10) Patent No.: US 8,303,788 B2
(45) Date of Patent: Nov. 6, 2012

(54) LIQUID ELECTROLYTE GAS SENSOR COMPRISING RIGID POROUS ELECTRODE SUPPORT

(75) Inventors: Martin Williamson, Poole (GB); David O'Grady, Gurteen (IR)

(73) Assignee: Honeywell Analytics AG, Uster (CH)

( * ) Notice: Subject to any disclaimer, the term of this patent is extended or adjusted under 35 U.S.C. 154(b) by 1052 days.

(21) Appl. No.: 10/591,188

(22) PCT Filed: Mar. 1, 2005

(86) PCT No.: PCT/GB2005/000765
§ 371 (c)(1),
(2), (4) Date: Sep. 19, 2008

(87) PCT Pub. No.: WO2005/085824
PCT Pub. Date: Sep. 15, 2005

(65) Prior Publication Data
US 2009/0008251 A1  Jan. 8, 2009

(30) Foreign Application Priority Data
Mar. 3, 2004  (EP) .................................. 04251228

(51) Int. Cl.
*G01N 27/413*  (2006.01)
(52) U.S. Cl. ......... 204/416; 204/415; 204/431; 204/432
(58) Field of Classification Search .................. 204/415, 204/431–432
See application file for complete search history.

(56) References Cited

U.S. PATENT DOCUMENTS

| | | | | |
|---|---|---|---|---|
| 4,017,373 A * | 4/1977 | Shaw et al. | | 204/432 |
| 4,406,770 A | 9/1983 | Chan et al. | | |
| 4,769,122 A * | 9/1988 | Marrese et al. | | 204/408 |
| 5,372,696 A * | 12/1994 | Kiesele et al. | | 204/416 |
| 6,410,189 B1 * | 6/2002 | Yamada et al. | | 429/233 |

FOREIGN PATENT DOCUMENTS

| | | |
|---|---|---|
| DE | 44 11 370 A | 10/1995 |
| EP | 0 496 527 | 7/1992 |
| EP | 0 780 686 A | 6/1997 |
| WO | WO 96/04550 A | 2/1996 |
| WO | WO 02/073177 A | 9/2002 |

OTHER PUBLICATIONS

Intl. Search Report dated May 30, 2005, Intl. Publ. No. WO 2005/085824 A1, published Sep. 15, 2005 International Searching Authority, European Patent Office.

* cited by examiner

*Primary Examiner* — Keith Hendricks
*Assistant Examiner* — Bach Dinh
(74) *Attorney, Agent, or Firm* — Husch Blackwell LLP

(57) ABSTRACT

An electrochemical gas sensor has a working electrode having a gas porous membrane and a catalyst layer formed on one side of the membrane; a counter electrode, electrolyte in contact with the catalyst both of the working electrode and of the counter electrode; and a support that is in contact with, and presses against the side of the working electrode remote from the electrolyte and that compresses the electrodes and the electrolyte together. The support includes open areas enabling gas to contact the membrane. The support provides a faster response and provides greater efficiency of catalyst usage.

19 Claims, 1 Drawing Sheet

Working: $2CO + 2H_2O \longrightarrow 2CO_2 + 4H^+ + 4e^-$

Counter: $4H^+ + 4e^- + 2O_2 \longrightarrow 2H_2O$

Working: $2CO + 2H_2O \longrightarrow 2CO_2 + 4H^+ + 4e^-$
Counter: $4H^+ + 4e^- + 2O_2 \longrightarrow 2H_2O$

LIQUID ELECTROLYTE GAS SENSOR COMPRISING RIGID POROUS ELECTRODE SUPPORT

The present application is a U.S national stage application of International Application No. PCT/GB2005/000765, filed Mar. 1, 2005, which International application was published on Sep. 15, 2005, under International Publication No. WO 2005/085824 A1. The International application claims priority of European Application No. 04251228.5, filed Mar. 3, 2004, and this application also claims the benefit of that date.

TECHNICAL FIELD

The present invention relates to electrochemical gas sensors for sensing gases and vapours in an atmosphere being monitored (herein called "target gases").

BACKGROUND ART

Electrochemical gas sensors are well known and are extensively used for the monitoring of various gases in an atmosphere, particularly toxic gases such as carbon monoxide and hydrogen sulphide, and also for the detection of oxygen.

Electrochemical gas sensors include the following components:
(a) a gas-permeable working (or sensing) electrode, where the target gas is either oxidised or reduced electrochemically in a half reaction; the electrode is normally made from a semi-permeable gas diffusion membrane, typically PTFE, having a layer of catalyst deposited on one of its surfaces;
(b) a counter electrode at which an electrochemical half-reaction takes place to balance the electrons generated or consumed by the half-reaction taking place at the working electrode; and
(c) a body of electrolyte in contact with both the working and counter electrodes.

The sensor is such that gas from the atmosphere being monitored is in contact with the working electrode.

The sensor may additionally include a reference electrode in contact with the electrolyte to define a stable potential that the working and counter electrodes can be referenced against.

In some electrochemical sensors, generally those sensors that detect target gases that can be tolerated in the atmosphere in a relatively large quantity, e.g. carbon monoxide, the sensor may include a gas access port that limits access of gas to the working electrode. The gas access port may be provided in a cap that forms the top of the gas sensor. For example, for a CO sensor cell detecting up to 1000 ppm, a gas access port of approximately 1 mm diameter can be used.

In other sensors, generally those sensors for poisonous target gases that can only be tolerated in the atmosphere in a relatively small quantity, e.g. arsine at 200 ppb, it is not desired to restrict the access of the atmosphere to the working electrode and a wide gas access port or no gas access port at all is provided so that the working electrode is essentially in direct contact with the atmosphere. Such sensors are advantageous in having a fast response time since the atmospheric gases need not diffuse through a gas access port in order to reach the working electrode.

The working electrode is typically a semi-permeable, flexible PTFE membrane having catalyst applied to the membrane surface in contact with the electrolyte. The working, counter and, if used, reference electrodes each needs to be maintained in intimate contact with the electrolyte and the catalytic surfaces of the electrodes should not be allowed to become uncovered otherwise unexpected current/voltage characteristics may occur. In practice, this condition is achieved by placing a porous material between at least the working and the counter electrodes, ensuring that sufficient electrolyte is maintained in the porous material between the various electrodes and compressing the electrode assembly, i.e. the electrodes and the intervening porous material, together.

Where the sensor includes a cap with a gas access port, this compressive force can be achieved by pressing the electrode assembly into a sensor housing by means of the cap, which is generally relatively rigid. The cap presses down on the electrode assembly either directly or indirectly via a porous mat. For sensor cells having a relatively small opening (e.g. a CO sensor with a 1 mm diameter port), the gas access port does not cause any problem with ensuring compression in the cell. However, for those gases (e.g. arsine), requiring a large gas access port, the port can almost be as large as the whole cap or indeed a cap may be dispensed with altogether. In this instance, even if a cap is provided, it can, at best, compress only the outer rim of the electrode assembly, causing the thin porous membrane of the working electrode, which is placed immediately under the cap, to bulge, stretch and, in extreme cases, even to split. In order to prevent this, it is necessary to use a rigid or semi-rigid support structure in the sensor that presses down on the electrode assembly independently of the cap. Generally, such support structures are made of moulded plastic that are at least 1 mm in thickness. In one commercially available electrochemical gas sensor, the structure takes the form of a cross with arms at least 1 mm deep and at least 1 mm wide, which forms part of the top or cap of the sensor cell. During the assembly of the sensor, the top or cap, with the cross, is bonded to the main body of the sensor such that the cross maintains the electrode assembly in compression.

We have discovered that, by replacing the cross-shaped frame with a thinner rigid or semi-rigid structure for supporting the working electrodes, several advantages can be obtained and previously unappreciated disadvantages avoided.

WO02/073177 discloses an electrochemical gas sensor having a working and counter electrode and an intervening body of electrolyte absorbed in a separator. A reservoir of electrolyte is also present that is absorbed in a wicking material that supplies electrolyte to the separator, thereby keeping the separator saturated with electrolyte. A cap with a gas access hole compresses the electrodes, the separator and the wicking material.

GB 2287791 discloses an electrochemical gas sensor having a working electrode, a counter electrode and a rigid porous ceramic body between the electrodes that is flooded with electrolyte. The working electrode is a rigid stainless steel gauze onto which a catalyst is fixed; its outer rim is bent over to fit in with other components of the sensor. A gas permeable membrane made of polymer resin it placed on top of the working electrode and finally a filter is provided made of PTFE coated stainless steel. The electrode and the porous ceramic body between the electrodes are rigid and so the whole assembly does not need to be supported. It is important for the filter to have a relatively closed structure so as to ensure that incoming gases come into contact with it and so are subject to its filtering action.

WO96/04550 describes an electrochemical gas sensor having a working electrode covered by a selective membrane that removes cross-sensitive gases, i.e. gases that the working electrode will react with but are not the gases that are being detected. In order to work, the selective membrane must be gas permeable and, if porous, will have only small holes through it.

DEFINITION OF INVENTION

According to the present invention, there is provided an electrochemical gas sensor comprising:
 a working electrode comprising a gas porous membrane and a catalyst layer formed on one side of the membrane;
 a counter electrode comprising a catalyst;
 electrolyte in contact with the catalyst both of the working electrode and of the counter electrode; and
 a rigid or semi-rigid support in contact with the side of the working electrode remote from the electrolyte, such support having a thickness of not greater than 0.5 mm, preferably less than 0.4 mm, more preferably less than 0.3 mm, e.g. less than 0.2 mm, wherein the support includes open areas allowing gas to contact the membrane, the surface area of the support between the open areas being less than 40%, preferably less than 30%, e.g. less than 20% and, most preferably, less than 10% of the total surface area of the support (including the open areas).

The sensor assembly beneath the support, including the electrodes and the intervening electrolyte, which is preferably absorbed in a porous material, is compressible and the support compresses the assembly to keep the components of the assembly in contact with each other and supports the assembly and prevents it expanding, which can cause the working electrode to deform or rupture.

The side of the support remote from the working electrode will be in gaseous contact with the atmosphere either directly or via a porous body.

The support will include solid regions, e.g. bars, between the open areas, the solid regions having a width of not greater than 0.5 mm, more preferably less than 0.3 mm, e.g. less than 0.2 mm;

Preferably, the support is metallic, e.g. stainless steel or nickel, and may optionally be coated with a chemically resistant material, e.g. PTFE, depending on the nature of the target gas. However, the material used for the support will be chosen to be inert to the target gas being detected and may be, for example, made of ceramic, plastics or reinforced resin material.

The bars between the open areas of the support are preferably formed into a pattern, most preferably a rectangular or hexagonal pattern, although other patterns are possible, e.g. mixed pentagons and squares. The areas of the bars should be kept to a minimum commensurate with providing sufficient strength to the support to allow it support the membrane of the working electrode and prevent it from bulging out to such an extent that it is liable to rupture.

The relative thinness of the support for the present invention, compared to the prior art, means that there is a smaller tendency for gas to become trapped in a pocket of gas in the immediate vicinity of the membrane; such gas pockets give rise to a diffusion barrier that target gas must cross before encountering the working electrode, thereby causing a slower response time in the sensor and a smaller signal. This is particularly evident (and hence disadvantageous) when the sensor has a low sensitivity to the target gas.

The use in the prior art of relatively wide bars, e.g. in the above-mentioned cross-shaped structure, covered a relatively large area of the working electrode. In contrast, the use of narrow bars (or other solid regions) between the open regions of the support means that a relatively low surface area of the membrane is covered with the bars. However, equally importantly, by using thin bars (or other solid regions), substantially the whole of the catalyst within the perimeter of the support can be accessed by target gas diffusing through the membrane. This arises since the gas tends to spread out in the course of migrating through the membrane and so catalyst underlying the edges of the bars can be accessed by the gas and, ultimately, if the bars are sufficiently thin, then the whole of the catalyst underlying the bars can be accessed by the gas. This more efficient use of catalyst within the working electrode allows the loading of catalyst on the working electrode to be reduced and/or the area of the working electrode to be reduced and/or results in an extended lifetime of the working electrode.

During its working life, the response of a sensor to a target gas will drift, which is generally thought to be due to the number of catalyst sites on the working electrode being reduced over time. The present invention makes more efficient use of the catalyst sites since fewer catalyst sites are occluded by the support as compared to the prior art. The greater availability of catalyst sites in the sensor of the present invention, because of the reduced occlusion by the support, provides a greater number of catalyst sites for a given catalyst loading and so extends the working life of a sensor; in other words, the drift of the sensor with time is less than the case of the prior art.

BRIEF DESCRIPTION OF DRAWINGS

The present invention will now be described by way of example only, by reference to the accompanying drawings in which:

FIG. 3 also includes a detailed view of two parts of the section A-A.

BEST MODE FOR CARRYING OUT INVENTION

Figure 1:
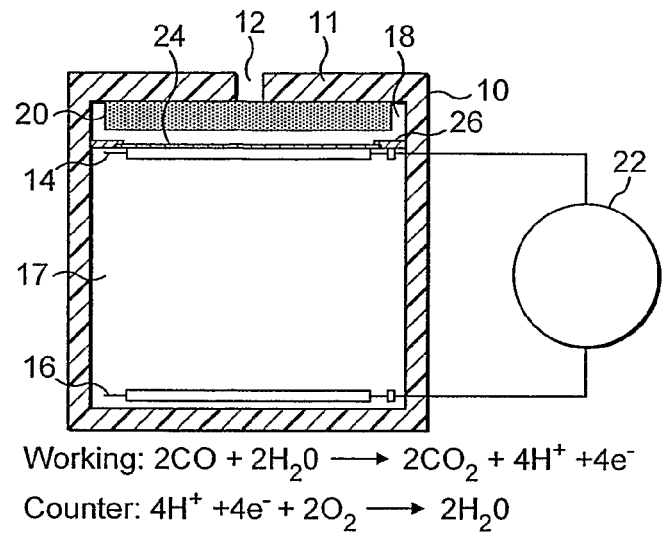
FIG. 1 is a schematic sectional view of an electrochemical gas sensor according to the present invention.

Referring initially to FIG. 1, there is shown a schematic sectional view of a sensor for monitoring a toxic gas, for example, carbon monoxide. The sensor includes a plastic moulded housing 10 having a cap 11, in which is formed a restricted opening 12 forming a gas access port for admission of gas from an atmosphere being monitored. Within the housing, working and counter electrodes 14, 16 are provided. Although not shown, the sensor may also include a reference electrode, as is well known in electrochemical gas sensor technology. A porous wick 17 containing absorbed electrolyte (typically concentrated (6M) sulphuric acid) is arranged between the working and the counter electrodes. The working and counter electrodes 14, 16 are each formed from a porous PTFE membrane (although the counter electrode membrane need not be porous), each having a catalyst layer on the side of the membrane facing the electrolyte. The membrane of the working electrode 14 is hydrophobic and prevents electrolyte from escaping through it while, at the same time, being microporous and allowing gas to migrate through it to the catalyst layer of the working electrodes. Therefore, a gas space 18 exists between the working electrode and the top of the housing 10. A highly porous filter 20, e.g. a carbon cloth, may be located within the gas space. The filter performs several functions; firstly, it can act as a gas spreader, spreading out the gas entering the sensor through the opening 12 across the width of the sensor, thereby allowing a more even spread of gas across the extent of the working electrode 14. Secondly, the filter can be such as to absorb contaminant gases that might react with the working electrode to give false readings.

If the target gas of the sensor is carbon monoxide, carbon monoxide is oxidised at the working electrode to carbon dioxide according to the half reaction shown in FIG. 1. Simultaneously, at the counter electrode, hydrogen ions are reduced to form water, as shown in FIG. 1. The working and counter electrodes 14, 16 are connected together through an external circuit 22 and, as a result of the half-reactions at the working and counter electrodes, current flows through the external circuit when target gas, e.g. carbon monoxide, is present in the atmosphere being monitored. The size of the current flowing will be depend on the amount of carbon monoxide reaching the working electrode, which in turn is proportional to the amount of carbon monoxide in the atmosphere being monitored. Therefore, the current flowing in the external circuit 22 provides a measure of the amount of carbon monoxide in the atmosphere.

The concentrated sulphuric acid electrolyte within the wick 17 can absorb water vapour from the atmosphere, thereby increasing its volume. Such an increase in volume would tend to push the working electrode 14 upwards into the gas space 18. This is resisted by a support 24, which is held by a ring 26, which in turn is welded to the sidewall of the housing 10 or (as described above) held in position by the top of the housing 10.

Figure 2:
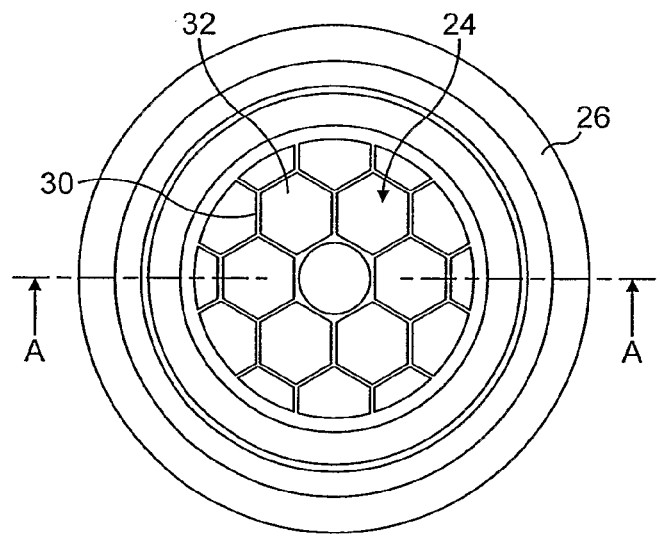
FIG. 2 is a plan view of the working electrode support of the sensor of FIG. 1.
Figure 3:
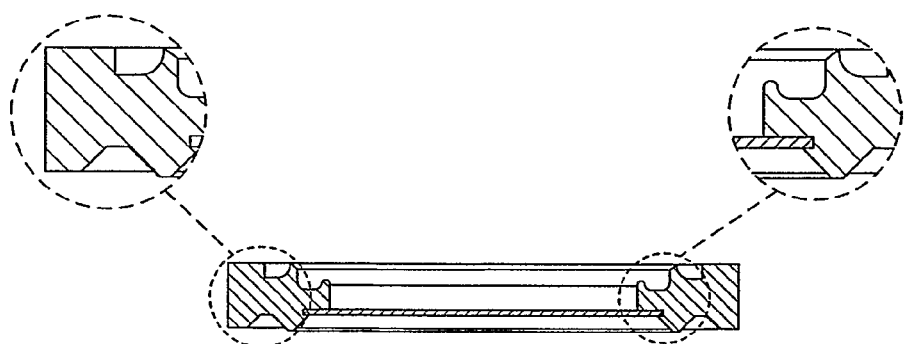
FIG. 3 is a sectional view along the lines A-A of FIG. 2.

The support and ring 24,26 are shown in greater detail in FIGS. 2 and 3. The support is in the form of a mesh 24, which is formed by bars 30, forming a series of hexagonal open regions or openings 32. The mesh is made of stainless steel that has been chemically etched to form the open regions 32. As will be appreciated, the material of the support mesh should be inert to the target gas and materials other than stainless steel can be used, e.g. nickel. The metallic support mesh may be coated, e.g. with PTFE. In addition, other manufacturing methods to form the support 24 are possible, e.g. laser cutting, punching and deburring, sandblasting and electrochemical forming. However, electrochemical etching is easy and relatively low cost to carry out and can be applied on an industrial scale.

The support mesh 24 formed by the opening 32 and the bars 30 is held at its edges by the ring 26, which can conveniently be achieved by insert moulding the ring around a pre-formed mesh.

The components of the sensor shown in FIG. 1 are compressed within the housing (the wick 17 being resilient) by the support 24, which holds the components in position and in particular holds the electrodes 14,16 against the wick and its absorbed electrolyte. The support 24 itself may be welded to the side of the sensor housing or the cap 11 may press against the ring 26 to provide the desired compression.

The mesh support 24 is only approximately 0.1 mm thick and accordingly does not entrap, to any substantial extent, gas within the openings 24 and hence does not form "dead spaces" where gas pockets form and through which gas from the atmosphere has to diffuse. In addition, the bars or struts 30 are only approximately 0.5 mm wide and accordingly do not mask substantial areas of the catalyst of the working electrode. Indeed, the bars 30 are so thin that the act of diffusing through the porous PTFE layer spreads the gas out to such an extent that catalyst lying directly underneath these bars or struts 30 will receive target gas. As can be seen, at least 95% of the area of the working electrode lying within the ring 26 is located in register with the openings 32. The use of such an open mesh to form the support 24 means that there is a substantially greater amount of catalyst available for reacting with target gas than was the case with prior art supports. Accordingly, as described above, the catalyst layer can be reduced and/or the size of the working electrode can be reduced.

In order to provide the necessary support to the working electrode, the support 24 is rigid or semi-rigid (by "semi-rigid" is meant that the support, though not absolutely rigid, still has an amount of stiffness that allows it to provide its support function). Supports that are able to flex are preferred since they allow a certain amount of expansion of the electrolyte and add robustness to the sensor cell against vibration, pressure changes and physical shock, e.g. being dropped.

The present invention is especially useful in sensors having either a low sensitivity to the target gas or a requirement to detect low concentrations of the target gas, and consequently have a large opening 12. The large opening 12 can extend nearly across the whole of the area of the top cap 11 or the cap can be dispensed with. Thus a sensor for a low concentration gas, e.g. arsine, would be essentially the same as that shown in FIG. 1, except that it would not have the cap 11 or the filter 20. In these circumstances, the response of the sensor is determined by the effective activity of the working electrode. The open structure of the support 24 allows the maximum exposure of the working electrode to gas diffusing into the sensor while still providing support for the working electrode. In addition, there are reduced "dead spaces" within the sensor providing further diffusion barriers for the diffusion of gas from the atmosphere to the working electrode. Also, because the support mesh 24 is relatively rigid, it can prevent the working electrode from bulging and possibly splitting even though the support is only anchored to the housing or the top 11 by means of the circumferential ring 26.

EXAMPLE

12 $H_2S$ sensors that are commercially available from Zellweger Analytics Limited under the trade mark SureCell were taken and each was modified by removing its cap with a gas access hole. Such SureCell sensors have a compressible electrode assembly made up of a working electrode in the form of PTFE sheet supporting a layer of catalyst, a reference electrode and a counter electrode; electrolyte absorbed in a porous material separates the working electrode form the reference and counter electrodes. The electrode assembly is held in a housing by a support in the form of a cross with arms 1 mm deep and 1 mm wide, which contacts the working electrode and compresses the electrode assembly into the housing.

The sensors were exposed to a test atmosphere containing hydrogen sulphide and the average current output of the 12 cells was 28.3 µA (2 standard deviations=1.2 µA).

A further batch of 12 $H_2S$ SureCell sensors were taken and each was modified by removing its cap with a gas access hole and the plastic cruciform support. In place of the plastic cruciform support, the support shown in FIGS. 2 and 3 was used, which has approximately 85% of its surface formed by the open areas, and the bars between the open areas are approximately 0.2 mm thick and 0.2 mm wide.

The sensors were exposed to same test atmosphere as the batch mentioned above and the average current output of the 12 cells was 53.9 µA (2 standard deviations=4.1 µA).

Accordingly it can be seen that the sensitivity of the sensors according to the present invention is about 1.9 times that of the sensors of the prior art.

The invention claimed is:

1. An electrochemical gas sensor comprising:
a working electrode comprising a gas porous membrane and a catalyst layer formed on one side of the membrane;
a counter electrode that includes a catalyst;
electrolyte in contact with the catalyst both of the working electrode and of the counter electrode; and
a support which is one of rigid or semi-rigid, the support defines a plurality of open areas allowing gas to contact the membrane, the support is in contact with, and presses against a side of the working electrode remote from the electrolyte to compress the electrodes and the electrolyte together, the support including solid regions that extend between the open areas for contacting and supporting the membrane, the support having a thickness of only approximately 0.1 mm thick and wherein the support defines a plurality of open areas allowing gas to contact the membrane, the surface area of the solid regions of the support between the open areas being less than 40% of the combined surface area of the open areas and the solid regions of the support between them.

2. A sensor as claimed in claim 1, wherein the solid regions of the support, between the open areas, are in the form of elongated members, having a width less than 0.5 mm.

3. A sensor as in claim 2 where the elongated members have a width less than one of 0.3 mm or 0.2 mm.

4. An electrochemical gas sensor comprising:
a working electrode comprising a gas porous membrane and a catalyst layer formed on one side of the membrane;
a counter electrode that includes a catalyst;
electrolyte in contact with the catalyst both of the working electrode and of the counter electrode; and
a support that is in contact with, and presses against a side of the working electrode displaced from the electrolyte to compress the electrodes and the electrolyte together, such support comprising a plurality of open areas that enable gas to contact the membrane, the support including solid regions that extend between the open areas for contacting and supporting the membrane, such solid regions having a thickness of only approximately 0.1 mm and having a width on the order of one of less than 0.3 mm, or less than 0.2 mm, and wherein the aggregate surface area of the solid regions is less than 40% of the combined surface area of the support, including the open areas.

5. A sensor as claimed in claim 4 wherein the support has a thickness of not greater than 0.5 mm.

6. A sensor as in claim 5 where the thickness is less than one of 0.4 mm, 0.3 mm or 0.2 mm.

7. A sensor as in claim 4 wherein the regions of the support between the open areas are in the form of elongated linear members.

8. A sensor as in claim 4 wherein the surface area of the support between the open areas is less than one of 30%, 20% or 10% of the surface area of the support.

9. A sensor as in claim 4 which includes a reference electrode.

10. A sensor as in claim 4 wherein the support is metallic.

11. A sensor as in claim 4 wherein the open areas of the support are formed into one of a rectangular or a hexagonal pattern.

12. A sensor as in claim 4 which includes a housing, and wherein the support includes a rim that is fused or welded to the housing.

13. An electrochemical gas sensor comprising:
a housing that defines an internal region;
first and second electrodes carried by the housing in the region;
an electrolyte between the electrodes;
a retaining mesh that is attached to the housing and is only approximately 0.1 mm thick, covering a predetermined area of one of the electrodes, the retaining mesh defines a plurality of open areas allowing gas to contact the one electrode, the retaining mesh includes solid regions that extend between the open areas and which presses the one electrode and the electrolyte toward the other electrode, the plurality of open areas of the mesh exceeds 60% of the area covered by the mesh.

14. A sensor as in claim 13 wherein the mesh is formed of elongated linear members having a width less than 0.5 mm.

15. A sensor as in claim 13 wherein the mesh has a thickness less than 0.5 mm.

16. A sensor as in claim 13 where the plurality of open areas of the mesh comprises a plurality of one of rectangular or hexagonal patterns.

17. A sensor as in claim 13 where the plurality of open areas of the mesh exceeds 70% of the area.

18. A sensor as in claim 17 where the electrodes are metallic and the mesh is flexible.

19. A sensor as in claim 13 where the plurality of open areas of the mesh exceeds 90% of the area.

* * * * *